United States Patent
Hasegawa et al.

(10) Patent No.: US 6,469,220 B2
(45) Date of Patent: Oct. 22, 2002

(54) TERTIARY ALCOHOL COMPOUNDS HAVING AN ALICYCLIC STRUCTURE

(75) Inventors: Koji Hasegawa, Niigata-ken (JP); Takeshi Kinsho, Niigata-ken (JP); Takeru Watanabe, Niigata-ken (JP)

(73) Assignee: Shin-etsu Chemical Co., Ltd. (JP)

( * ) Notice: Subject to any disclaimer, the term of this patent is extended or adjusted under 35 U.S.C. 154(b) by 0 days.

(21) Appl. No.: 10/025,064

(22) Filed: Dec. 19, 2001

(65) Prior Publication Data

US 2002/0087033 A1 Jul. 4, 2002

(30) Foreign Application Priority Data

Dec. 25, 2000 (JP) ........................ 2000-391867

(51) Int. Cl.$^7$ .............................................. C07C 35/22
(52) U.S. Cl. ........................................ 568/820; 568/817
(58) Field of Search .................. 568/817, 820

(56) References Cited

U.S. PATENT DOCUMENTS 4,128,509 A * 12/1978 Schleppnik
2002/0009668 A1 * 1/2002 Nishimura

FOREIGN PATENT DOCUMENTS

WO  WO-00/67072 A  * 11/2000
WO  WO-01/63362 A  *  8/2001

* cited by examiner

Primary Examiner—Michael L. Shippen

(74) Attorney, Agent, or Firm—Myers Bigel Sibley & Sajovec, P.A.

(57) ABSTRACT

The present invention provides novel tertiary alcohol compounds which are useful as monomers for the preparation of photoresist materials having high transparency and a great affinity for the substrate and hence suitable for use in photolithography using a light source comprising preferably light having a wavelength of 300 nm or less and more preferably light emitted from an ArF excimer laser.

Specifically, the present invention provides tertiary alcohols compounds represented by the following general formula (1):

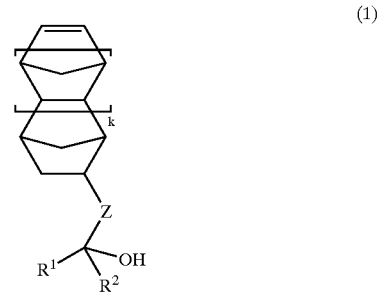

(1)

wherein $R^1$ and $R^2$ each independently represent a straight-chain, branched or cyclic alkyl group having 1 to 10 carbon atoms, in which some or all of the hydrogen atoms on the constituent carbon atoms may be replaced by a halogen atom or halogen atoms, or $R^1$ and $R^2$ may be joined together to form an aliphatic hydrocarbon ring; Z represents a straight-chain, branched or cyclic divalent organic group having 2 to 10 carbon atoms; and k is 0 or 1.

9 Claims, No Drawings

TERTIARY ALCOHOL COMPOUNDS HAVING AN ALICYCLIC STRUCTURE

CROSS-REFERENCE TO RELATED APPLICATIONS

The present application claims priority to Japanese Patent Application No. 2000-391867, filed Dec. 25, 2000.

BACKGROUND OF THE INVENTION

1. Field of the Invention

This invention relates to novel tertiary alcohol compounds which are useful as monomers for the preparation of base resins for chemical amplification resist materials suitable for use in fine processing techniques.

2. Description of the Related Art

In recent years, increasingly finer pattern rules are required as the degree of integration and speed of LSIs become higher. Under these circumstances, far ultraviolet lithography is regarded as a promising fine processing technique of the next generation. In particular, photolithography using KrF or ArF excimer laser light as the light source is considered to be a technique indispensable for ultrafine processing to a size of 0.3 µm or less, and its realization is eagerly desired.

With regard to resist materials for use in photolithography using excimer laser tight (in particular, ArF excimer laser light having a wavelength of 193 nm) as the light source, it is required that they not only have high transparency at the relevant wavelength, but also have high etching resistance which allows a reduction in film thickness, high sensitivity which does not overload the expensive materials of the optical system, and among others, high resolving power which permits fine patterns to be accurately formed. In order to meet these requirements, it is essential to develop a base resin having high transparency, high rigidity and high reactivity. However, no polymer having all of these characteristics is known at present. Thus, the existing state of the art is that no resist material suitable for practical use is available as yet.

As highly transparent resins, copolymers of acrylic acid or methacrylic acid derivatives, polymers containing an alicyclic compound derived from a norbornene derivative in the main chain, and the like are known, but none of them are satisfactory. For example, it is relatively easy to enhance the reactivity of copolymers of acrylic acid or methacrylic acid derivatives, because highly reactive monomers may be freely introduced thereinto or acid-labile units may be arbitrarily increased. However, the structure of the main chain makes it very difficult to enhance its rigidity. On the other hand, the rigidity of polymers containing an alicyclic compound in the main chain is within acceptable limits. However, their reactivity cannot be easily enhanced because, owing to the structure of the main chain, their reactivity with acid is lower than that of poly(meth)acrylates and their latitude in polymerization is low. In addition, they also have the disadvantage that, when they are applied to a substrate, their adhesion is poor because of the high hydrophobicity of the main chain. Consequently, when resist materials are prepared by using these polymers as base resins, the result will be such that they have sufficient sensitivity or resolving power, but cannot withstand etching, or they have acceptable etching resistance, but their sensitivity and resolving power are too low for practical purposes. As used herein, the term "(meth)acrylate" means a methacrylate or an acrylate.

SUMMARY OF THE INVENTION

The present invention has been made in view of the above-described circumstances, and an object thereof is to provide novel tertiary alcohol compounds which are useful as monomers for the preparation of photoresist materials having high transparency and a great affinity for the substrate and hence suitable for use in photolithography using a light source comprising preferably light having a wavelength of 300 nm or less and more preferably light emitted from an ArF excimer laser.

The present inventors carried out intensive investigations with a view to accomplishing the above object, and have now found that tertiary alcohol compounds represented by the following general formula (1) can be obtained in high yield and with simplicity by employing any of the processes which will be described later, and that resins prepared by using these tertiary alcohol compounds have high transparency at the exposure wavelength of an excimer laser and resist materials using them as base resins exhibit high resolving power and good adhesion to the substrate.

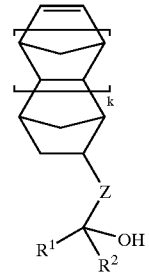

(1)

wherein $R^1$ and $R^2$ each independently represent a straight-chain, branched or cyclic alkyl group having 1 to 10 carbon atoms, in which some or all of the hydrogen atoms on the constituent carbon atoms may be replaced by a halogen atom or halogen atoms, or $R^1$ and $R^2$ may be joined together to form an aliphatic hydrocarbon ring; Z represents a straight-chain, branched or cyclic divalent organic group having 2 to 10 carbon atoms; and k is 0 or 1.

Resist materials prepared by using polymers obtained by polymerization of the tertiary alcohol compounds of the present invention are sensitive to high-energy radiation, having good adhesion to the substrate, high sensitivity, high resolving power and high etching resistance, and are useful for fine processing with electron rays or far ultraviolet radiation. In particular, since they exhibit low absorption at the exposure wavelengths of ArF and KrF excimer lasers, they can easily form fine patterns perpendicular to the substrate and are hence suitable for use as fine pattern forming materials for the manufacture of VLSI (very large scale integration).

DETAILED DESCRIPTION OF THE PREFERRED EMBODIMENTS

The present invention will be more specifically described hereinbelow.

The tertiary alcohol compounds of the present invention are represented by the general formula (1).

$R^1$ and $R^2$ each independently represent a straight-chain, branched or cyclic alkyl group having 1 to 10 carbon atoms, in which some or all of the hydrogen atoms on the constituent carbon atoms may be replaced by a halogen atom or halogen atoms. Specific examples thereof include methyl, ethyl, n-propyl, isopropyl, n-butyl, sec-butyl, tert-butyl, tert-amyl, n-pentyl, n-hexyl, cyclopentyl, cyclohexyl, bicyclo[2.2.1]heptyl, bicyclo[2.2.2]octyl, bicyclo[3.3.1]nonyl, bicyclo[4.4.0]decanyl, adamantyl, trifluoromethyl, 2,2,2-trifluoroethyl, 2,2,2-trichloroethyl, 3,3,3-trifluoropropyl and 3,3,3-trichloropropyl. Alternatively, $R^1$ and $R^2$ may be joined together to form an aliphatic hydrocarbon ring. Specific examples of the ring so formed include cyclobutane, cyclopentane, cyclohexane, bicyclo[2.2.1]heptane, bicyclo[2.2.2]octane, bicyclo[3.3.1]nonane, bicyclo[4.4.0]decane and adamantane. Z represents a straight-chain, branched or cyclic divalent organic group having 2 to 10 carbon atoms. Specific examples thereof include ethylene, propane-1,1-diyl, propane-1,2-diyl, propane-1,3-diyl, butane-1,1-diyl, butane-1,2-diyl, butane-1,3-diyl, butane-1,4-diyl, pentane-1,1-diyl, pentane-1,2-diyl, pentane-1,3-diyl, pentane-1,4-diyl, pentane-1,5-diyl, hexane-1,1-diyl, hexane-1,2-diyl, hexane-1,3-diyl, hexane-1,4-diyl, hexane-1,5-diyl, hexane-1,6-diyl, cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl and cyclohexane-1,4-diyl. k is 0 or 1.

Among the tertiary alcohol compounds represented by the general formula (1), tertiary alcohol compounds represented by the following general formula (2) are especially preferred.

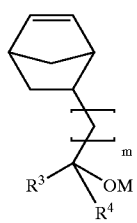
(2)

wherein $R^3$ and $R^4$ each independently represents a straight-chain, branched or cyclic alkyl group having 1 to 6 carbon atoms, or $R^3$ and $R^4$ may be joined together to form an aliphatic hydrocarbon ring; and m is an integer satisfying the conditions defined by $3 \leq m \leq 6$.

In this formula, $R^3$ and $R^4$ each independently represent a straight-chain, branched or cyclic alkyl group having 1 to 6 carbon atoms. Specific examples thereof include methyl, ethyl, n-propyl, isopropyl, n-butyl, sec-butyl, tert-butyl, tert-amyl, n-pentyl, n-hexyl, cyclopentyl and cyclohexyl.

Specific examples of the tertiary alcohol compounds represented by the above general formulas (1) and (2) are as follows:

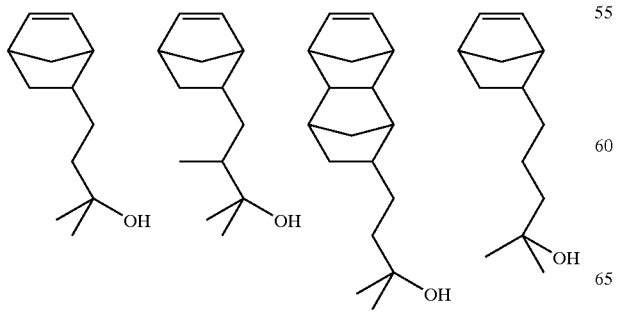

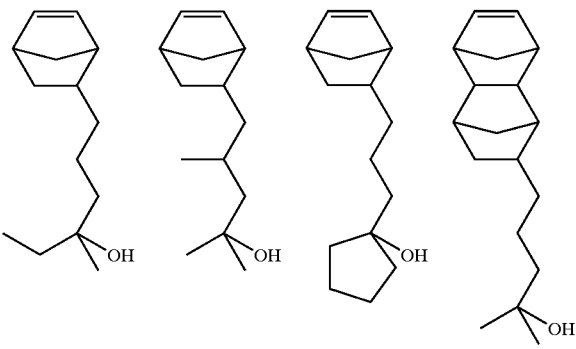

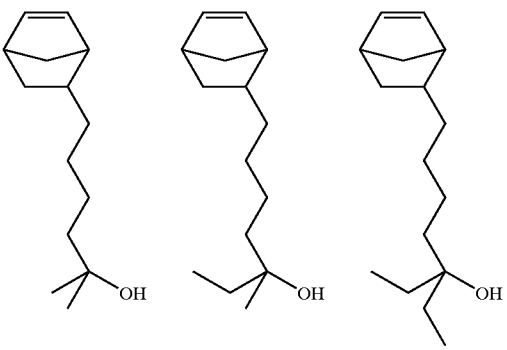

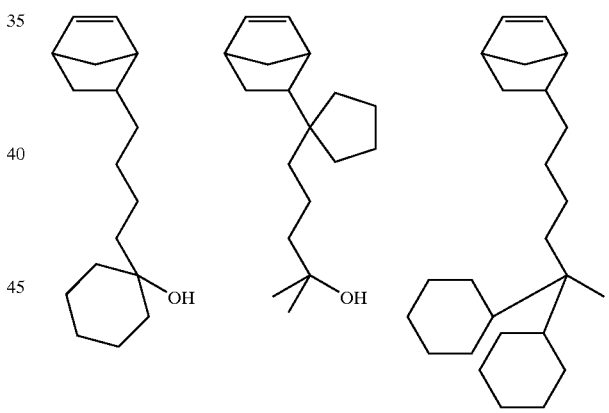

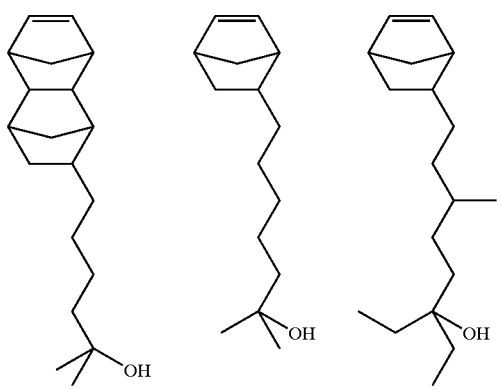

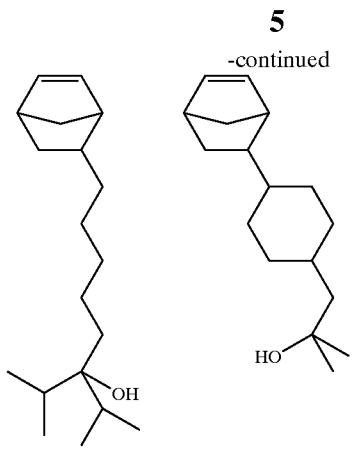

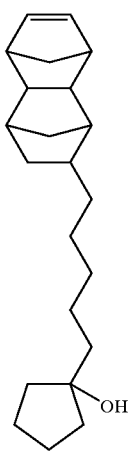

It is believed that, in resist polymers formed by using these compounds as monomers, the tertiary alcoholic hydroxyl group which is considered to be a polar group for the development of adhesion can be located at a position remote from the main chain of the polymer through the intervention of a linker [i.e., —Z— in formula (1)], and this permits the polymer to exhibit good adhesion to the substrate. Moreover, the lipophilicity of the polymer as a whole can be suitably regulated by choosing a compound having an appropriate number of carbon atoms with respect to k, $R^1$, $R^2$ and Z in the formula and using it as a raw material for the formation of the polymer. Thus, it is believed that the dissolution characteristics of the polymer can also be controlled.

The tertiary alcohol compounds of formula (1) in accordance with the present invention may be prepared, for example, according to any of the following four processes. However, it is to be understood that their preparation processes are not limited thereto. These preparation processes are specifically described below.

(A) As a first process, a desired tertiary alcohol compound (1) can be synthesized by the nucleophilic addition reaction of an organometallic reagent (3) to a ketone compound (4).

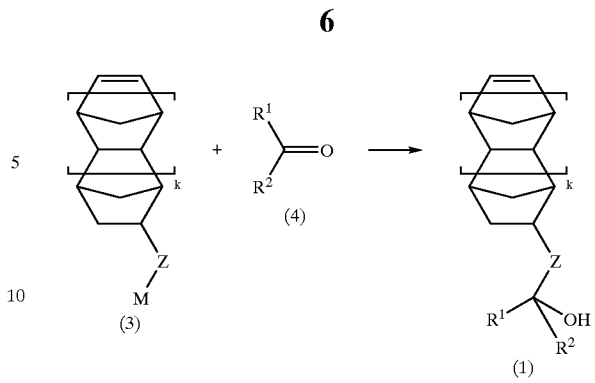

wherein $R^1$, $R^2$, Z and k are as defined above, M represents Li, Na, K, MgP or ZnP, and P represents a halogen atom.

It is desirable that the organometallic reagent (3) be used in an amount of 0.5 to 2.0 moles, preferably 0.9 to 1.2 moles, per mole of the ketone compound (4). Preferred examples of the solvent include ethers such as tetrahydrofuran, diethyl ether, di-n-butyl ether and 1,4-dioxane; and hydrocarbons such as n-hexane, n-heptane, benzene, toluene, xylene and cumene. These solvents may be used alone or in admixture. The reaction temperature and the reaction time may vary widely according to the reaction conditions. For example, when a Grignard reagent (of formula (3) in which M is MgP) is used as the organometallic reagent, the reaction temperature is in the range of −20 to 80° C. and preferably 0 to 50° C. As to the reaction time, it is desirable from the viewpoint of yield to bring the reaction to completion while tracing it by gas chromatography (GC) or silica gel thin-layer chromatography (TLC). However, the reaction time usually ranges from about 0.5 to about 10 hours. The desired tertiary alcohol compound (1) can be isolated from the reaction mixture by an ordinary aqueous work-up. If necessary, the compound may further be purified according to common techniques such as distillation and chromatography.

(B) As a second process, a desired tertiary alcohol compound (1) can be synthesized by the nucleophilic addition reaction of an organometallic reagent (5) to a ketone compound (6).

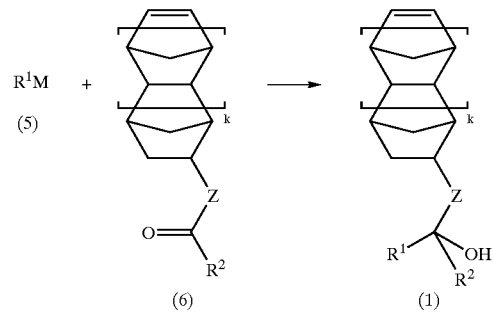

wherein $R^1$, $R^2$, Z, k and M are as defined above.

It is desirable that the organometallic reagent (5) be used in an amount of 1.0 to 3.0 moles, preferably 1.1 to 1.5 moles, per mole of the ketone compound (6). Preferred examples of the solvent include ethers such as tetrahydrofuran, diethyl ether, di-n-butyl ether and 1,4-dioxane; and hydrocarbons such as n-hexane, n-heptane, benzene, toluene, xylene and cumene. These solvents may be used alone or in admixture. The reaction temperature and the reaction time may vary widely according to the reaction conditions. For example, when a Grignard reagent (of formula (5) in which M is MgP)

is used as the organometallic reagent, the reaction temperature is in the range of −20 to 80° C. and preferably 0 to 50° C. As to the reaction time, it is desirable from the viewpoint of yield to bring the reaction to completion while tracing it by gas chromatography (GC) or silica gel thin-layer chromatography (TLC). However, the reaction time usually ranges from about 0.5 to about 10 hours. The desired tertiary alcohol compound (1) can be isolated from the reaction mixture by an ordinary aqueous work-up. If necessary, the compound may further be purified according to common techniques such as distillation and chromatography.

(C) As a third process, a desired tertiary alcohol compound (1) can be synthesized by the nucleophilic addition reaction of organometallic reagents (5) and (7) to an ester compound (8).

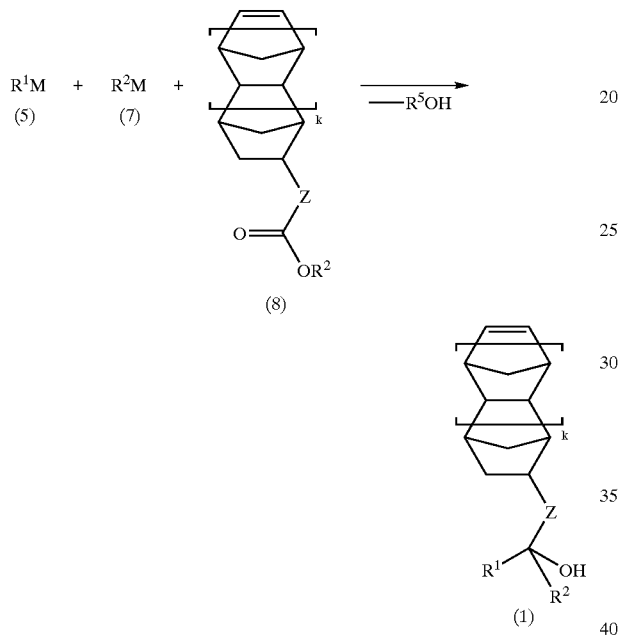

which $R^1$ and $R^2$ are joined together to form an aliphatic hydrocarbon ring (i.e., the partial structural formula

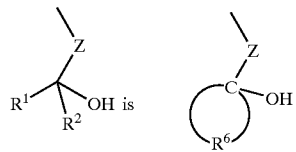

wherein $R^6$ is a divalent hydrocarbon group produced when $R^1$ and $R^2$ are joined together to form an aliphatic hydrocarbon ring), this tertiary alcohol compound (1) can be synthesized by the nucleophilic addition reaction of an organometallic reagent (9) to an ester compound (8).

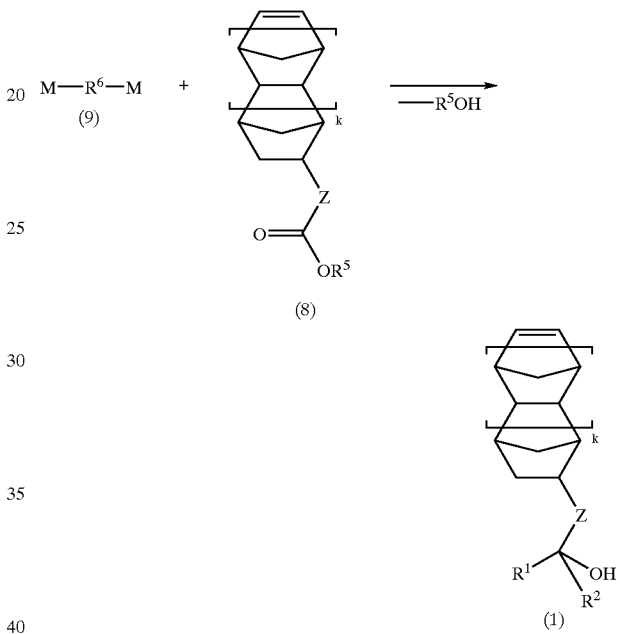

wherein $R^1$, $R^2$, Z, k and M are as defined above, and $R^5$ represents an alkyl group such as methyl or ethyl.

It is desirable that the organometallic reagents (5) and (7) be used in an amount of 2.0 to 5.0 moles, preferably 2.0 to 3.0 moles, per mole of the ester compound (8). Preferred examples of the solvent include ethers such as tetrahydrofuran, diethyl ether, di-n-butyl ether and 1,4-dioxane; and hydrocarbons such as n-hexane, n-heptane, benzene, toluene, xylene and cumene. These solvents may be used alone or in admixture. The reaction temperature and the reaction time may vary widely according to the reaction conditions. For example, when Grignard reagents (of formulas (5) and (7) in which M is MgP) are used as the organometallic reagents, the reaction temperature is in the range of 0 to 100° C. and preferably 20 to 70° C. As to the reaction time, it is desirable from the viewpoint of yield to bring the reaction to completion while tracing it by gas chromatography (GC) or silica gel thin-layer chromatography (TLC). However, the reaction time usually ranges from about 0.5 to about 10 hours. The desired tertiary alcohol compound (1) can be isolated from the reaction mixture by an ordinary aqueous work-up. If necessary, the compound may further be purified according to common techniques such as distillation and chromatography.

(D) As a fourth process, when the desired tertiary alcohol compound is represented by the general formula (1) in wherein $R^1$, $R^2$, $R^5$, $R^6$, Z, k and M are as defined above.

It is desirable that the organometallic reagent (9) be used in an amount of 1.0 to 3.0 moles, preferably 1.1 to 1.5 moles, per mole of the ester compound (8). Preferred examples of the solvent include ethers such as tetrahydrofuran, diethyl ether, di-n-butyl ether and 1,4-dioxane; and hydrocarbons such as n-hexane, n-heptane, benzene, toluene, xylene and cumene. These solvents may be used alone or in admixture. The reaction temperature and the reaction time may vary widely according to the reaction conditions. For example, when a Grignard reagent (of formula (9) in which M is MgP) is used as the organometallic reagent, the reaction temperature is in the range of 0 to 100° C. and preferably 20 to 70° C. As to the reaction time, it is desirable from the viewpoint of yield to bring the reaction to completion while tracing it by gas chromatography (GC) or silica gel thin-layer chromatography (TLC). However, the reaction time usually ranges from about 0.5 to about 10 hours. The desired tertiary alcohol compound (1) can be isolated from the reaction mixture by an ordinary aqueous work-up. If necessary, the compound may further be purified according to common techniques such as distillation and chromatography.

When a polymer is formed by using a tertiary alcohol compound of the present invention as a monomer, it is common practice to mix the aforesaid monomer with a solvent, add a catalyst or a polymerization initiator, and subject the resulting mixture to a polymerization reaction while heating or cooling it as required. This polymerization may be carried out according to any conventional polymerization technique. Examples of the aforesaid polymerization include ring-opening metathesis polymerization, addition polymerization, and alternating copolymerization with maleic anhydride or a maleimide. In some cases, the aforesaid monomer may be copolymerized with another norbornene type monomer, a (meth)acrylate type monomer or the like.

Resist materials may generally be prepared by using the polymer obtained in the above-described manner as a base polymer and adding an organic solvent and an acid generator thereto. If necessary, a crosslinking agent, a basic compound, a dissolution inhibitor and the like may also be added thereto. Such resist materials may be prepared in the usual manner.

The present invention is more specifically explained with reference to the following synthesis examples, reference example and comparative reference example. However, these examples are not to be construed to limit the scope of the invention.

SYNTHESIS EXAMPLES

Tertiary alcohol compounds in accordance with the present invention were synthesized according to the formulations described below.

Synthesis Example 1

Synthesis of 2-Methyl-6-(5-norbornen-2-yl)hexan-2-ol (monomer 1)

A Grignard reagent was prepared from 95.5 g of 1-chloro-4-(5-norbornen-2-yl)butane, 13.3 g of magnesium, and 200 ml of anhydrous tetrahydrofuran. Then, under an atmosphere of nitrogen, 35.5 g of acetone was added thereto at 40° C. over a period of 1 hour. After this mixture was stirred for 1 hour, the reaction product was hydrolyzed by the addition of an aqueous solution of ammonium chloride, followed by separation into aqueous and organic phases. Subsequently, the organic phase was washed with water and a saturated aqueous solution of sodium chloride, dried over anhydrous sodium sulfate, and concentrated under reduced pressure. The resulting residue was purified by vacuum distillation to obtain 90.5 g of 2-methyl-6-(5-norbornen-2-yl)hexan-2-ol (boiling point: 93–98° C./66 Pa; yield: 87%).

IR (thin film): $\nu$=3371, 3058, 2966, 2933, 2863, 1465, 1380, 1379, 1377, 1336, 1253, 1203, 1186, 1151, 906, 833, 825, 769, 717 cm$^{-1}$; $^1$H-NMR of major isomer (300 MHz in CDCl$_3$): $\delta$=0.44–0.50 (1H, m), 1.03–1.12 (2H, m), 1.16(6H, s), 1.22–1.46 (9H, m), 1.77–1.85 (1H, m), 1.91–2.01 (1H, m), 2.70–2.76 (2H, m), 5.86–5.93 (1H, m), 6.06–6.11 (1H, m).

Synthesis Example 2

Synthesis of 3-Methyl-7-(5-norbornen-2-yl)heptan-3-ol (monomer 2)

3-Methyl-7-(5-norbornen-2-yl)heptan-3-ol (boiling point: 106–110° C./53 Pa; yield: 88%) was obtained in the same manner as in Synthesis Example 1, except that 2-butanone was used in place of acetone. IR (thin film): $\nu$=3380, 3058, 2966, 2935, 2863, 1461, 1373, 1336, 1270, 1253, 1178, 1149, 993, 929, 904, 879, 833, 775, 717 cm$^{-1}$; $^1$H-NMR of major isomer (300 MHz in CDCl$_3$): $\delta$=0.42–0.51 (1H, m), 0.87 (3H, t), 1.03–1.09 (2H, m), 1.12(3H, s), 1.16–1.51 (11H, m), 1.77–1.85 (1H, m), 1.93–2.01 (1H, m), 2.70–2.76 (2H, m), 5.86–5.92 (1H, m), 6.06–6.11 (1H, m).

Synthesis Example 3

Synthesis of 3-Ethyl-7-(5-norbornen-2-yl)heptan-3-ol (monomer 3)

3-Ethyl-7-(5-norbornen-2-yl)heptan-3-ol (boiling point: 118–121° C./53 Pa; yield: 89%) was obtained in the same manner as in Synthesis Example 1, except that 3-pentanone was used in place of acetone.

IR (thin film): $\nu$=3403, 3058, 2964, 2935, 2863, 1569, 1459, 1394, 1376, 1336, 1253, 1149, 944, 833, 825, 769, 717 cm$^{-1}$; $^1$H-NMR of major isomer (300 MHz in CDCl$_3$): $\delta$=0.42–0.51 (1H, m), 0.84 (6H, t), 1.01–1.48 (15H, m), 1.77–1.85 (1H, m), 1.93–2.02 (1H, m), 2.70–2.76 (2H, m), 5.87–5.92 (1H, m), 6.07–6.11 (1H, m).

Synthesis Example 4

Synthesis of 2-Methyl-7-(5-norbornen-2-yl)heptan-2-ol (monomer 4)

2-Methyl-7-(5-norbornen-2-yl)heptan-2-ol (boiling point: 118–121° C./66 Pa; yield: 91%) was obtained in the same manner as in Synthesis Example 1, except that 1-chloro-5-(5-norbornen-2-yl)pentane was used in place of 1-chloro-4-(5-norbornen-2-yl)butane.

IR (thin film): $\nu$=3363, 3058, 2966, 2931, 2863, 2852, 1569, 1465, 1380, 1336, 1251, 1199, 1182, 1151, 904, 835, 769, 717 cm$^{-1}$; $^1$H-NMR of major isomer (300 MHz in CDCl$_3$): $\delta$=0.44–0.50 (1H, m), 0.96–1.12 (2H, m), 1.18 (6H, s), 1.20–1.47 (11H, m), 1.77–1.85 (1H, m), 1.90–2.01 (1H, m), 2.70–2.76 (2H, m), 5.86–5.92 (1H, m), 6.07–6.11 (1H, m).

Synthesis Example 5

Synthesis of 1-{4-(5-Norbornen-2-yl)-1-butyl}cyclohexanol (monomer 5)

1-{4-(5-Norbornen-2-yl)-1-butyl}cyclohexanol (yield: 89%) was obtained in the same manner as in Synthesis Example 1, except that cyclohexanone was used in place of acetone.

Synthesis Example 6

Synthesis of 2-Methyl-6-(5-norbornen-2-yl)-6,6-tetramethylenehexan-2-ol (monomer 6)

2-Methyl-6-(5-norbornen-2-yl)-6,6-tetramethylenehexan-2-ol (yield: 84%) was obtained in the same manner as in Synthesis Example 1, except that 1-chloro-4-(5-norbornen-2-yl)-4,4-tetramethylenebutane was used in place of 1-chloro-4-(5-norbornen-2-yl)butane.

Synthesis Example 7

Synthesis of 2-Methyl-4-(5-norbornen-2-yl)butan-2-ol (monomer 7)

2-Methyl-4-(5-norbornen-2-yl)butan-2-ol (yield: 89%) was obtained in the same manner as in Synthesis Example 1, except that 1-chloro-2-(5-norbornen-2-yl)ethane was used in place of 1-chloro-4-(5-norbornen-2-yl)butane.

Synthesis Example 8

Synthesis of 2,3-Dimethyl-4-(5-norbornen-2-yl)butan-2-ol (monomer 8)

2,3-Dimethyl-4-(5-norbornen-2-yl)butan-2-ol (yield: 90%) was obtained in the same manner as in Synthesis Example 1, except that 2-chloro-1-(5-norbornen-2-yl) propane was used in place of 1-chloro-4-(5-norbornen-2-yl) butane.

Synthesis Example 9

Synthesis of 2-Methyl-4-(8-tetracyclo-[4.4.0.1$^{2,5}$.1$^{7,10}$]dodecen-3-yl)butan-2-ol (monomer 9)

2-Methyl-4-(8-tetracyclo[4.4.0.1$^{2,5}$.1$^{7,10}$]dodecen-3-yl)-butan-2-ol (yield: 83%) was obtained in the same manner as in Synthesis Example 1, except that 1-chloro-2-(8-tetracyclo [4.4.0.1$^{2,5}$.1$^{7,10}$]dodecen-3-yl)ethane was used in place of 1-chloro-4-(5-norbornen-2-yl)butane.

Synthesis Example 10

Synthesis of 2-Methyl-5-(5-norbornen-2-yl)pentan-2-ol (monomer 10)

2-Methyl-5-(5-norbornen-2-yl)pentan-2-ol (yield: 89%) was obtained in the same manner as in Synthesis Example 1, except that 1-chloro-3-(5-norbornen-2-yl)propane was used in place of 1-chloro-4-(5-norbornen-2-yl)butane.

Synthesis Example 11

Synthesis of 1-{3-(5-Norbornen-2-yl)-propyl}cyclopentanol (monomer 11)

1-{3-(5-Norbornen-2-yl)propyl}cyclopentanol (yield: 86%) was obtained in the same manner as in Synthesis Example 1, except that cyclopentanone and 1-chloro-3-(5-norbornen-2-yl)propane were used in place of acetone and 1-chloro-4-(5-norbornen-2-yl)butane, respectively.

Synthesis Example 12

Synthesis of 2-Methyl-6-(8-tetracyclo[4.4.0.1$^{2,5}$.1$^{7,10}$]dodecen-3-yl)hexan-2-ol (monomer 12)

2-Methyl-6-(8-tetracyclo[4.4.0.1$^{2,5}$.1$^{7,10}$]dodecen-3-yl) hexan-2-ol (yield: 82%) was obtained in the same manner as in Synthesis Example 1, except that 1-chloro-4-(8-tetracyclo [4.4.0. 1$^{2,5}$.1$^{7,10}$]dodecen-3-yl)butane was used in place of 1-chloro-4-(5-norbornen-2-yl)butane.

Synthesis Example 13

Synthesis of 1,1-Diisopropyl-6-(5-norbornen-2-yl) hexanol (monomer 13)

1,1-Diisopropyl-6-(5-norbornen-2-yl)hexanol (yield: 85%) was obtained in the same manner as in Synthesis Example 1, except that diisopropyl ketone and 1-chloro-5-(5-norbornen-2-yl)pentane were used in place of acetone and 1-chloro-4-(5-norbornen-2-yl)butane, respectively.

Synthesis Example 14

Synthesis of 1,1-Dicyclopentyl-6-(5-norbornen-2-yl) hexanol (monomer 14)

1,1-Dicyclopentyl-6-(5-norbornen-2-yl)hexanol (yield: 85%) was obtained in the same manner as in Synthesis Example 1, except that dicyclopentyl ketone and 1-chloro-5-(5-norbornen-2-yl)pentane were used in place of acetone and 1-chloro-4-(5-norbornen-2-yl)butane, respectively.

Synthesis Example 15

Synthesis of 1-{5-(8-tetracyclo[4.4.0.1$^{2,5}$.1$^{7,10}$] dodecen-3-yl)pentyl}cyclopentanol (monomer 15)

1-{5-(8-Tetracyclo[4.4.0.1$^{2,5}$.1$^{7,10}$]dodecen-3-yl)pentyl}-cyclopentanol (yield: 82%) was obtained in the same manner as in Synthesis Example 1, except that cyclopentanone and 1-chloro-5-(8-tetracyclo[4.4.0.1$^{2,5}$.1$^{7,10}$] dodecen-3-yl) pentane were used in place of acetone and 1-chloro-4-(5-norbornen-2-yl)butane, respectively.

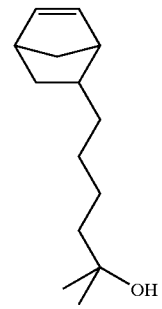

(monomer 1)

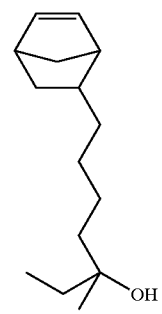

(monomer 2)

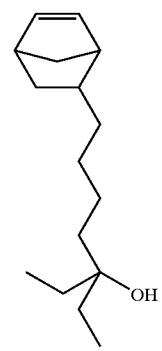

(monomer 3)

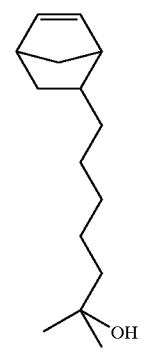

(monomer 4)

(monomer 5)
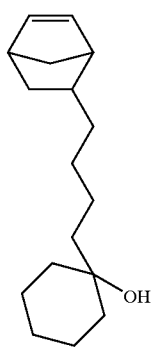
(monomer 6)
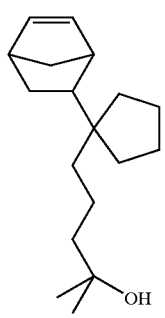
(monomer 7)
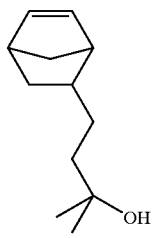
(monomer 8)
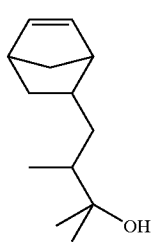
(monomer 9)
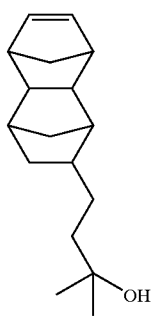
(monomer 10)
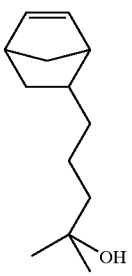
(monomer 11)
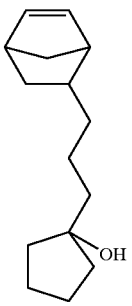
(monomer 12)
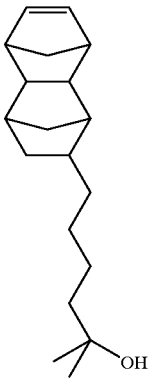
(monomer 13)
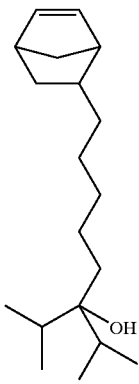

-continued

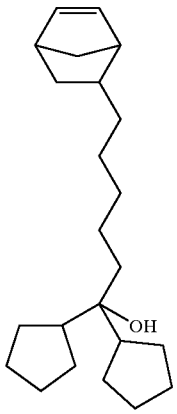

(monomer 14)

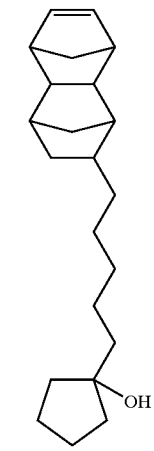

(monomer 15)

Reference Example

A polymer was synthesized by using one of the tertiary alcohol compounds obtained in the foregoing Synthesis Examples. Then, a resist material was prepared by incorporating this polymer compound as a base resin, and its adhesion to the substrate was examined.

Using V60, manufactured by Wako Pure Chemical Industries Ltd.) as an initiator, tert-butyl 5-norbornene-2-carboxylate, monomer 1 and maleic anhydride were polymerized to obtain an alternating copolymer of tert-butyl 5-norbornene-2-carboxylate, 2-methyl-6-(5-norbornen-2-yl) hexan-2-ol and maleic anhydride (in a copolymerization ratio of 4:1:5). Using this polymer, a resist material was prepared so as to have the composition described below. After a silicon wafer was sprayed with hexamethyldisilazane at 90° C. for 40 seconds, the above resist material was spin-coated onto the silicon wafer and then heat-treated at 110° C. for 90 seconds to form a resist film having a thickness of 500 nm. This silicon wafer was exposed to light from a KrF excimer laser, heat-treated at 110° C. for 90 seconds, and then developed by soaking it in a 2.38% aqueous solution of tetramethylammonium hydroxide for 60 seconds. Thus, 1:1 line-and-space patterns were formed. When the developed wafer was observed by top-down SEM, it was confirmed that patterns having a size of down to 0.26 μm did not peel off but remained on the wafer.

The composition of the resist material was as follows.
Base resin: 80 parts by weight.
Acid generator: Triphenylsulfonium trifluoromethanesulfonate, 1.0 part by weight.
Solvent: Propylene glycol monomethyl ether acetate, 480 parts by weight.
Others: Tri-n-butylamine, 0.08 part by weight.

Comparative Reference Example

For purposes of comparison, an alternating copolymer of tert-butyl 5-norbornene-2-carboxylate and maleic anhydride (in a copolymerization ratio of 1:1) was used to prepare a resist material having the same composition as in the above-described Reference Example. This resist material was exposed under the same conditions as described above and its adhesion to the substrate was evaluated. As a result, it was found that no pattern having a size of 0.50 μm or less remained.

It has been confirmed by the above-described results that polymers prepared by using the tertiary alcohol compounds of the present invention as raw materials have much better adhesion to the substrate, as compared with conventional polymers.

What is claimed is:

1. A tertiary alcohol compound represented by the following general formula (1):

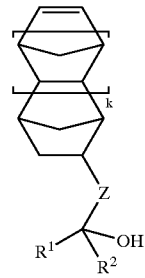

wherein $R^1$ and $R^2$ each independently represents a straight-chain, branched or cyclic alkyl group having 1 to 10 carbon atoms, or $R^1$ and $R^2$ may be joined together to form an aliphatic hydrocarbon ring; Z represents a straight-chain, branched or cyclic divalent alkyl group having 2 to 10 carbon atoms; and k is 0 or 1.

2. A tertiary alcohol compound as claimed in claim 1 which is represented by the following general formula (2):

(2)

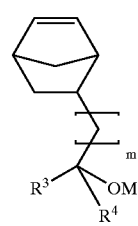

wherein $R^3$ and $R^4$ each independently represents a straight-chain, branched or cyclic alkyl group having 1 to 6 carbon atoms, or $R^3$ and $R^4$ may be joined together to form an aliphatic hydrocarbon ring; and m is an integer satisfying the conditions defined by $3 \leq m \leq 6$.

3. A tertiary alcohol compound as claimed in claim 1 wherein $R^1$ and $R^2$ are each independently selected from the group consisting of methyl, ethyl, n-propyl, isopropyl, n-butyl, sec-butyl, tert-butyl, tert-amyl, n-pentyl, n-hexyl, cyclopentyl, cyclohexyl, bicyclo[2.2.1]heptyl, bicyclo[2.2.2]octyl, bicyclo[3.3.1]nonyl, bicyclo[4.4.0]decanyl, and adamantyl.

4. A tertiary alcohol compound as claimed in claim 1 wherein $R^1$ and $R^2$ are joined together to form an aliphatic hydrocarbon ring.

5. A tertiary alcohol compound as claimed in claim 4 wherein the aliphatic hydrocarbon ring is selected from the group consisting of cyclobutane, cyclopentane, cyclohexane, bicyclo[2.2.1]heptane, bicyclo[2.2.2]octane, bicyclo[3.3.1]nonane, bicyclo[4.4.0]decane, and adamantane.

6. A tertiary alcohol compound as claimed in claim 1 wherein Z is selected from the group consisting of ethylene, propane-1,1-diyl, propane-1,2-diyl, propane-1,3-diyl, butane-1,1-diyl, butane-1,2-diyl, butane-1,3-diyl, butane-1,4-diyl, pentane-1,1-diyl, pentane-1,2-diyl, pentane-1,3-diyl, pentane-1,4-diyl, pentane-1,5-diyl, hexane-1,1-diyl, hexane-1,2-diyl, hexane-1,3-diyl, hexane-1,4-diyl, hexane-1,5-diyl, hexane-1,6-diyl, cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, and cyclohexane-1,4-diyl.

7. A tertiary alcohol compound as claimed in claim 1 wherein k is 0.

8. A tertiary alcohol compound as claimed in claim 1 wherein k is 1.

9. A tertiary alcohol compound as claimed in claim 2 wherein $R^3$ and $R^4$ are independently selected from the group consisting of methyl, ethyl, n-propyl, isopropyl, n-butyl, sec-butyl, tert-butyl, tert-amyl, n-pentyl, n-hexyl, cyclopentyl, and cyclohexyl.

* * * * *

UNITED STATES PATENT AND TRADEMARK OFFICE
CERTIFICATE OF CORRECTION

PATENT NO.     : 6,469,220 B2
DATED          : October 22, 2002
INVENTOR(S)    : Hasegawa et al.

It is certified that error appears in the above-identified patent and that said Letters Patent is hereby corrected as shown below:

<u>Title page,</u>
Item [57], ABSTRACT,
In the line appearing immediately after formula (1), the portion of the sentence reading "independently represent a straih-chain, branched" should read -- independently represents a straight-chain, branched --.

<u>Column 1,</u>
Line 1, which reads "TERTIARY ALCOHOL COMPOUNDS" should read
-- NOVEL TERTIARY ALCOHOL COMPOUNDS --

<u>Column 3,</u>
Line 30, the formula appears as:

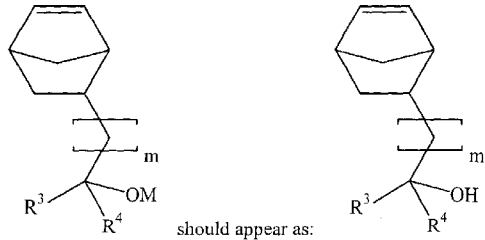

<u>Column 4,</u>
Line 35, the rightmost formula appear as:

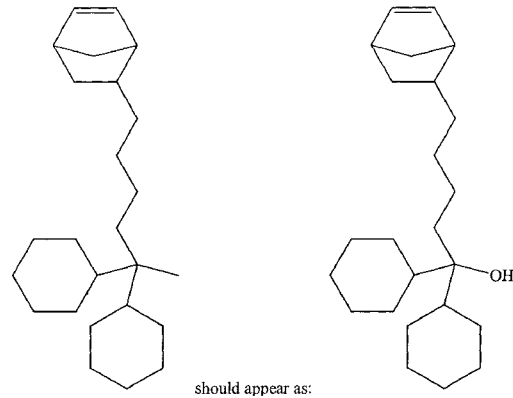

UNITED STATES PATENT AND TRADEMARK OFFICE
CERTIFICATE OF CORRECTION

PATENT NO.    : 6,469,220 B2
DATED         : October 22, 2002
INVENTOR(S)   : Hasegawa et al.

It is certified that error appears in the above-identified patent and that said Letters Patent is hereby corrected as shown below:

Column 16,
Line 40, formula (2) appears as:

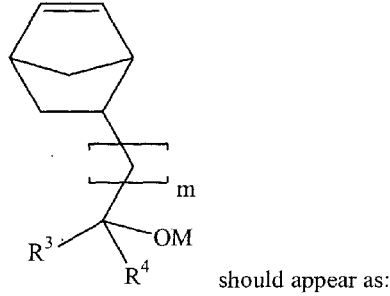   should appear as:   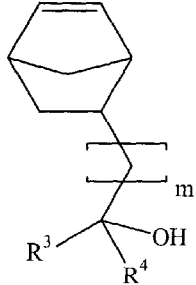

Signed and Sealed this

Twenty-ninth Day of July, 2003

JAMES E. ROGAN
*Director of the United States Patent and Trademark Office*